United States Patent [19]

Lee

[11] Patent Number: 4,655,226
[45] Date of Patent: Apr. 7, 1987

[54] DISPOSABLE BIOPSY NEEDLE UNIT

[75] Inventor: Peter F. Lee, Edina, Minn.

[73] Assignee: Southland Instruments, Inc., Minneapolis, Minn.

[21] Appl. No.: 684,129

[22] Filed: Dec. 20, 1984

Related U.S. Application Data

[63] Continuation-in-part of Ser. No. 562,272, Dec. 16, 1983, abandoned.

[51] Int. Cl.$^4$ ............................................. A61B 10/00
[52] U.S. Cl. ..................................................... 128/754
[58] Field of Search ............... 128/749, 751, 752, 753, 128/754, 305

[56] References Cited

U.S. PATENT DOCUMENTS

| | | |
|---|---|---|
| 798,093 | 8/1905 | Dean . |
| 1,039,591 | 9/1912 | Prideaux . |
| 1,718,596 | 6/1929 | Smith . |
| 2,198,666 | 4/1940 | Gruskin . |
| 2,295,849 | 9/1942 | Kayden . |
| 2,472,116 | 6/1949 | Maynes . |
| 2,660,342 | 11/1953 | Ruf . |
| 2,705,494 | 4/1955 | Broadwin . |
| 2,735,427 | 2/1956 | Sullivan . |
| 2,863,452 | 12/1958 | Ogle, Sr. . |
| 3,598,108 | 8/1971 | Jamshidi et al. . |
| 3,628,524 | 12/1971 | Jamshidi . |
| 3,819,091 | 6/1974 | Hollender . |
| 3,882,849 | 5/1975 | Jamshidi . |
| 3,938,505 | 2/1976 | Jamshidi . |
| 4,163,446 | 8/1979 | Jamshidi .................... 128/754 |
| 4,262,676 | 4/1981 | Jamshidi .................... 128/753 |
| 4,266,555 | 5/1981 | Jamshidi .................... 128/753 |
| 4,314,565 | 2/1982 | Lee .............................. 128/753 |
| 4,356,828 | 11/1982 | Jamshidi .................... 128/754 |
| 4,366,822 | 1/1983 | Altshuler .................... 128/753 |
| 4,469,109 | 9/1984 | Mehl ........................... 128/753 |

Primary Examiner—William E. Kamm
Attorney, Agent, or Firm—Merchant, Gould, Smith, Edell, Welter & Schmidt

[57] ABSTRACT

An improved disposable biopsy needle unit (12) includes a metal cannula (16), a molded plastic T-shaped handle (18), and a removable stylet (20). A solid hub portion (28) of the handle (18) is formed around a lateral tab (30) near the proximal end of the cannula (16) for reinforcement. A hollow fitting (32) extends between the proximal end of the cannula (16) and a recess between the opposite wing portions (26) of the handle (18). Locking ears (48) are preferably provided on the fitting (32) for releasable attachment to an aspiration device, such as a syringe (14). The stylet (20) includes a solid needle (34) with a turned proximal end within a molded plastic cap (38) for reinforcement. A lug (44) and slot (46) are provided on the stylet (20) and handle (18), respectively, for properly locating the stylet when inserted into the cannula (16). A second embodiment (80) incorporates an upset, non-circular boss (82) on the fitting (32') instead of a tab (30) on the cannula (16') for internal reinforcement.

10 Claims, 9 Drawing Figures

DISPOSABLE BIOPSY NEEDLE UNIT

CROSS-REFERENCE TO RELATED APPLICATION

This application is a continuation-in-part of copending application Ser. No. 562,272 filed Dec. 16, 1983, abandoned.

TECHNICAL FIELD

The present invention relates generally to a biopsy needle unit. More particularly, this invention concerns an improved biopsy needle unit of sturdy and safe but inexpensive construction which is adapted for limited reuse or disposal after a single use.

BACKGROUND ART

Biopsy specimens can be obtained by surgical excision or needle biopsy procedures. In general, a needle biopsy procedure involves inserting a cannula-and-stylet assembly through an incision until the tip of the assembly is at or near the site from which a biopsy specimen is desired. After positioning of the assembly, the stylet is withdrawn and the cannula is inserted further to collect a specimen in its distal end. Suction is then applied to the proximal end of the cannula, usually by means of a conventional syringe, to obtain or assist in severing the specimen for subsequent histologic and/or cytologic examination in a laboratory.

Such biopsy specimens can be utilized to diagnose a wide variety of diseases. For example, there are over one hundred forms of cancer, which is the second leading cause of death in the United States, and fluid, tissue and bone marrow biopsies are widely utilized to diagnose and treat some forms of cancer. It will thus be appreciated that the quick retrieval of such specimens with minimal discomfort and trauma to the patient is important to the success of such procedures.

A variety of biopsy needle units have been available heretofore. In general, such units include an outer cannula or hollow needle with a removable inner needle and/or solid stylet extending therethrough. Some releasable locking means is generally provided for securing the inner needle and/or the stylet in longitudinal position within the outer needle. For example, U.S. Pat. Nos. 4,356,828; 4,266,555; 4,262,676; 3,628,524; and 3,598,108 to Jamshidi are representative of the prior art in this area. Such devices, however, require re-sterilization after each use and also require re-sharpening after a few uses, and thus tend to be relatively expensive.

As a result, various attempts have been made to develop biopsy needle units which are partially or completely disposable. For example, my prior U.S. Pat. No. 4,314,565 shows a biopsy needle unit wherein the needle is removably secured by a threaded collar in the chuck of a generally T-shaped stainless steel handle. This unit utilizes a replaceable needle, which can be sterilized and sharpened for reuse, or disposed of after each use, but the handle still requires sterilization after each use.

Completely disposable biopsy needle units have been available heretofore, however, these have not been altogether satisfactory either. Such units tend to incorporate stainless steel needles with plastic handles which in turn is a critical stress junction. Breakage or slippage at this junction during insertion of the needle can cause injury to the patient. Similarly, breakage or slippage at the junction between the solid stylet and its end cap can cause injury to the doctor performing the precedure. It will be appreciated that considerable pushing and twisting forces are applied to such devices during use, particularly while obtaining bone marrow specimens.

Some of the disposable biopsy needle units of the prior art have been of three-piece construction with a separate cover cap for securing the stylet in place, which cap can be difficult to remove particularly with gloved hands. For example, disposable bone marrow biopsy/aspiration needles of this type are available from Monoject division of Sherwood Medical of St. Louis, Missouri. U.S. Pat. No. 4,258,722, to Sessions is also representative of the prior art in this regard.

Other biopsy needle units of the prior art have been of two-piece construction, but with other drawbacks. For example, U.S. Pat. No. 4,469,109 to Mehl shows such a two-piece unit; however, the stylet is secured to the needle by means of a button-and-spring detent locking-groove that requires a twisting motion to engage or disengage, which can be inconvenient if not awkward with gloved hands. A converging bore is provided for receiving the end of a syringe for aspiration, but no means are provided for quickly and conveniently securing the syringe and needle together. As a result, the doctor usually requires an assistant to complete the procedure.

A need has thus arisen for an improved disposable biopsy needle unit of inexpensive but safe, secure, and reliable construction which is also comfortable and easy to manipulate by one person.

SUMMARY OF INVENTION

The present invention comprises a disposable biopsy needle unit which overcomes the foregoing and other difficulties associated with the prior art. Two embodiments are disclosed. In accordance with the first embodiment of the invention, there is provided a disposable biopsy needle unit comprising a stainless steel cannula or hollow needle having a tapered, bevelled distal end adapted for insertion into tissue or bone. The proximal end of the needle is secured to a molded plastic handle of generally T-shape. The handle includes a pair of flanged hollow wings extending in opposite lateral directions from the tapered solid hub. The hub of the handle is molded around a transverse metal tab secured near the proximal end of the needle for reinforcement to to stabilize the needle against slippage or breakage relative to the handle. The proximal end of the needle is connected to a tapered female fitting extending through to the opposite side of the handle and opening into a recess between the wings. A solid stylet with a bevelled distal end is removably inserted into the needle and a plastic cap is molded on the proximal end of the stylet, which is preferably turned at about a right angle for reinforcement and safety purposes. A lug is provided on the cap for receipt in a hole in the handle for proper rotational positioning of the stylet within the needle. Locking ears are preferably provided on the needle fitting for releasably engaging corresponding structure on the barrel of a single hand-controlled aspiration syringe like that shown in the parent hereof so the biopsy needle/aspiration unit can be easily manipulated by one person.

In accordance with a second embodiment, the hub of the handle is molded around the adjoining ends of the needle and fitting, which has an upset, non-circular integral boss portion instead of a separate tab, for reinforcement to stabilize the needle against slippage or breakage relative to the handle.

BRIEF DESCRIPTION OF DRAWINGS

A better understanding of the invention can be had by reference to the following Detailed Description in conjunction with the acompanying Drawings wherein.

DETAILED DESCRIPTION

Figure 1:
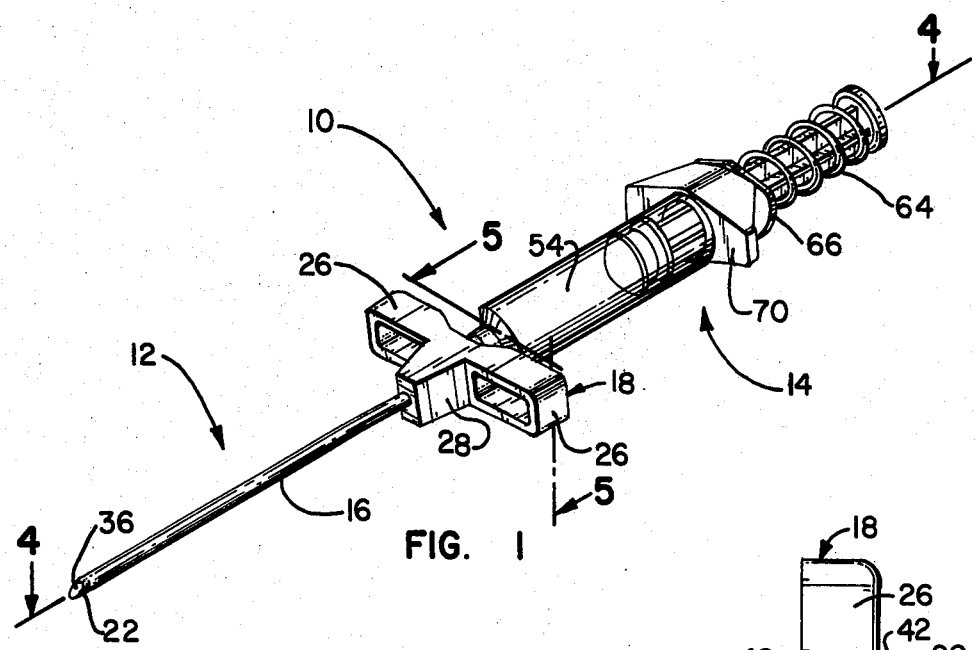
FIG. 1 is a perspective view of the disposable biopsy needle/aspiration unit incorporating the invention.

Referring now to the Drawings, wherein like reference numerals designate like or corresponding elements throughout the views, and particularly referring to FIG. 1, there is shown a disposable biopsy needle/aspiration syringe assembly 10 incorporating the invention. The assembly 10 includes a disposable biopsy needle unit 12 for obtaining a fluid, tissue, or bone marrow specimen from a patient, together with a single hand-controlled syringe 14 which can be releasably connected in end-to-end relationship to the needle for retrieving the specimen by aspiration for laboratory examination. Two embodiments of the needle unit are disclosed. As will be explained more fully hereinafter, the disposable biopsy needle/aspiration syringe assembly 10 is of improved construction for better structural integrity, reliability, safety, and ease of manipulation.

Figure 2:
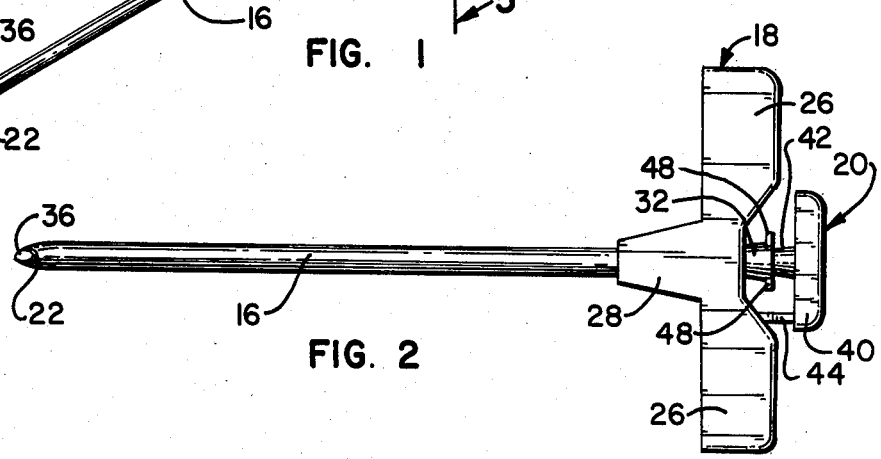
FIG. 2 is an enlarged plan view of the disposable biopsy needle unit of the first embodiment herein.
Figure 3:
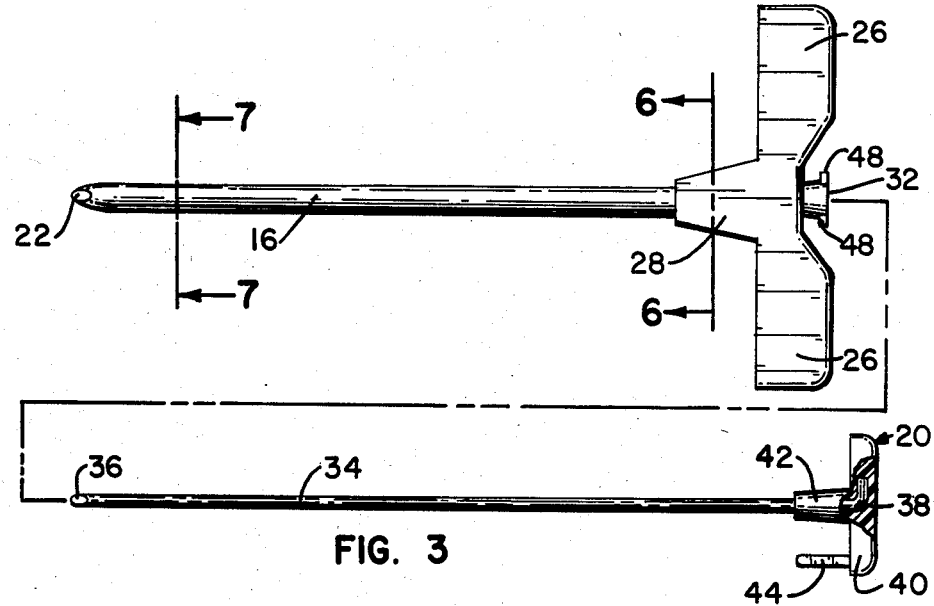
FIG. 3 is an exploded plan view (partially cutaway) of the disposable biopsy needle unit herein.
Figure 4:
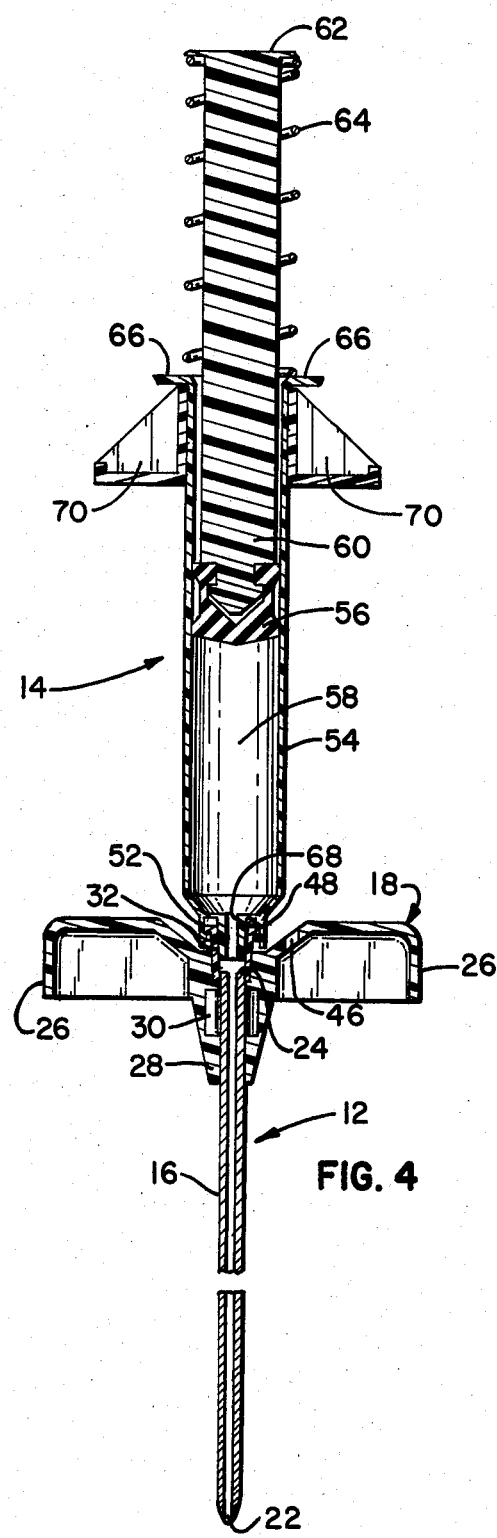
FIG. 4 is a sectional view taken generally along lines 4—4 of FIG. 1 in the direction of the arrows.

The constructional details of the disposable biopsy needle unit 12 of the first embodiment, are best shown in FIGS. 2 through 4. The biopsy needle unit 12 comprises a straight cannula or hollow needle 16 secured to a generally T-shaped handle 18 with a removable stylet 20 extending into the needle. The needle 16 is preferaby formed of stainless steel and is of substantially hollow cylindrical configuration throughout the major portion of its length to define a uniform longitudinal bore therethrough. The needle 16 includes an open distal end 22 and an open proximal end 24. The distal end 22 of the needle 16 is preferably bevelled and externally tapered as shown to facilitate insertion into a patient and to the specimen site.

The handle 18 is of generally T-shaped configuration and is preferably formed of suitable molded plastic capable of autoclaving for initial sterilization. In particular, the handle 18 includes a pair of flanged hollow wings 26 extending in opposite lateral directions from a solid hub 28 molded about the proximal end of the needle 16. The distal surfaces of wings 26 are open and angular while the proximal surfaces are closed and rounded, for better comfort and control by the doctor during a biopsy procedure. In accordance with the preferred construction, a metal tab 30 is externally secured to the needle 16 near its proximal end 24, preferably by means of laser welding. This comprises a significant feature of the present invention because it provides reinforcement and stabilization at the critical junction between the needle 16 and handle 18 to prevent any relative longitudinal or rotational movement therebetween during insertion of the biopsy needle unit 12.

A tapered female Luer fitting 32 extends between the proximal end 24 of the needle 16 and a recess provided between the inner ends of the wings 26 of handle 18. The fitting 32 serves as a receiver and connection for the stylet 20 or the hub of the aspiration syringe 14, as will be explained more fully hereinafter. The provision of a tapered female fitting 32 in recessed position within the handle 18 also comprises a significant feature of the present invention because it eliminates point-pressure on the handle of the doctor after removal of stylet 20 and if the needle unit 12 must then be inserted further. The fitting 32 can be formed of either suitable plastic or metal, and is secured in tight fluid communication with the proximal end 24 of the needle 16 by means of a friction fit. The handle 18 is thus molded about tab 30, a portion of the fitting 32, and a portion of needle 16 adjacent its proximal end 24.

The removable stylet 20 comprises a straight needle 34 of substantially uniform solid cylindrical configuration through its length. The needle 34 is preferably of stainless steel and includes a bevelled distal end 36 and a turned proximal end 38 molded within a solid plastic cap 40. The proximal end 38 of the stylet needle 34 is preferably turned at about a right angle as shown. The use of a stylet needle 34 having a turned proximal end comprises an important feature of the invention because this reinforces the junction between the needle and the cap against longitudinal loadings, which are reacted primarily through the hand of the doctor during insertion of the needle unit 12 into the patient.

The cap 40 includes a rounded proximal side for engaging the doctor's hand, and a flat distal side. A tapered stem 42 extends from distal side of cap 40 and is adapted for snug engagement in the fitting 32 of the handle 18. In addition, a locating lug 44 is provided on the same side of cap 40 for receipt in a slot 46 of the handle 18 when the stylet 20 is inserted inside the needle 16 so that the bevelled proximal ends 36 and 22 thereof are substantially even to close the end of the needle unit 12 and are oriented in the same plane to present a substantially smooth end surface during insertion. Thus, the stylet needle 34 is rotationally-oriented by lug 44 and slot 46, but is retained in longitudinal position within the outer hollow needle 16 by the hand of the doctor gripping unit 12 during insertion. After insertion and release of the doctor's grip, the stylet 20 can be withdrawn directly without additional manipulation to release any detent or the like. This also comprises an important feature of the invention.

Figure 5:
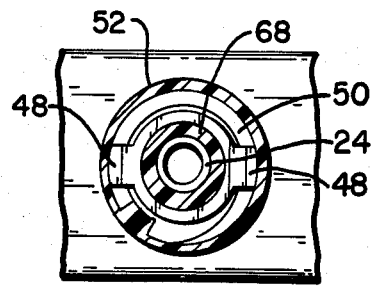
FIG. 5 is an enlarged sectional view taken generally along lines 5—5 of FIG. 1 in the direction of the arrows.
Figure 6:
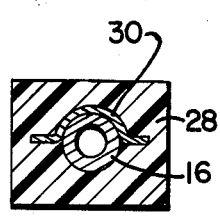
FIGS. 6 and 7 are enlarged sectional views taken generally along lines 6—6 and lines 7—7, respectively, of FIG. 3 in the direction of the arrows.
Figure 7:

In accordance with the preferred construction, the disposable biopsy needle 12 is adapted for releasable locking engagement with an aspiration device such as syringe 14. In particular, a pair of opposite laterally-extending locking ears 48 are provided on the proximal end of the Luer fitting 32. The locking ears 48 are adapted for engagement with threads 50 formed on the inside of a collar 52 on the end of the syringe 14, as is best seen in FIGS. 4 and 5. This enables the disposable biopsy needle unit 12 and the syringe 14 to be releasably secured in end-to-end, fluid tight relationship to facilitate manipulation by a single person. This too comprises a significant feature of the invention. In all other respects, the syringe 14 is constructed substantially similar to the single hand-controlled syringe disclosed and claimed in my co-pending parent application.

Briefly, the syringe 14 comprises a hollow barrel 54 with a gasket 56 movable therein to define a chamber with a variable control volume 58. The gasket 56 is connected to a plunger 60 extending beyond the barrel 54. An even cap or pressure plate 62 is provided on the external end of the plunger 60, and a compression spring 64 is disposed around the plunger between the pressure plate and the flared end of the barrel 54 defining a pair of opposite laterally-extending finger grips 66. A tapered hub 68 is provided at the other end of the barrel 54 for snug engagement with the fitting 32 of the biopsy needle unit 12. The biopsy needle unit 12 and syringe 14 are screwed together by means of locking ears 48 and threads 50. If desired, supplemental finger grips 70 can be provided on the barrel 54 to suit the hand size of the user.

After the biopsy needle unit 12 has been inserted into the patient in the usual manner, and the stylet 20 has been withdrawn from needle 16, the syringe 14 can then be easily secured to the end of the fitting 32. One hand of the doctor is employed to stabilize the biopsy needle 16. The other hand holds syringe 14 while compressing spring 64 and attaching the syringe to the fitting 32 with a twisting motion. Without removing or repositioning either hand, relaxation of the grip on the syringe 14 enables spring 64 to draw the plunger 60 outwardly so that the biopsy specimen can be aspirated into or through the needle 16 for subsequent examination. The syringe 14 can then be removed with another twisting motion, as the other hand holds the needle unit 12. A more comprehensive explanation of the operation of the single hand-controlled syringe 14 can be found in my co-pending parent application.

Figure 8:
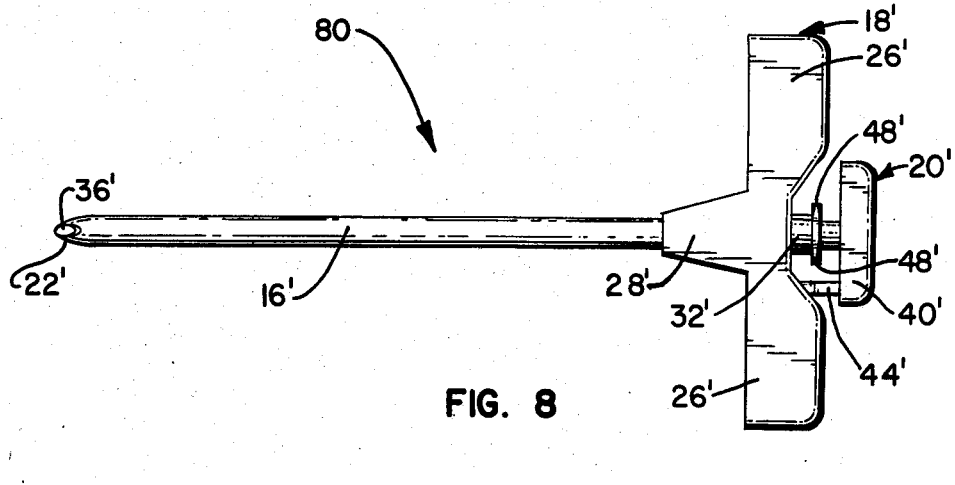
FIG. 8 is an enlarged plan view of the disposable biopsy needle unit of the second embodiment herein.
Figure 9:
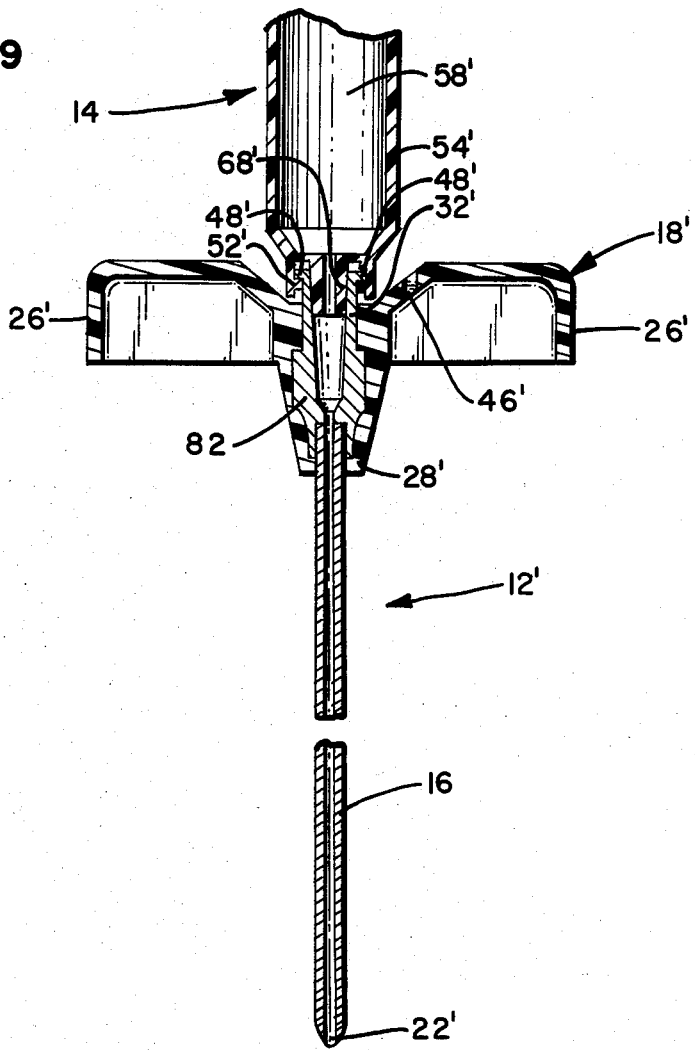
FIG. 9 is a sectional view similar to FIG. 4, but showing internal constructional details of the second embodiment.

FIGS. 8 and 9 shows a disposable biopsy needle unit 80 incorporating a second embodiment of the invention. The biopsy needle 80 incorporates numerous components which are substantially identical in construction and function to corresponding components of the biopsy needle unit 12. These components have been designated with the same reference numerals utilized in connection with unit 12, but have been differentiated therefrom with prime (') notations.

The primary distinction between the two embodiments comprises the fact that, whereas the needle unit 12 incorporates a separate tab 30 for additional reinforcement within the hub 28 of handle 18, the biopsy needle unit 80 instead incorporates a relatively longer Luer fitting 32' having an upset, non-circular external boss portion 82 thereon. In accordance with the preferred construction, the fitting 32' and the upset, non-circular boss portion 82 are of integral metal construction laser-welded to the proximal end of the hollow needle 16' so as to obtain essentially the same advantages with one less part and thus simpler construction. Except for elimination of the transverse tab 30 and incorporation of the upset, non-circular boss portion 82 directly onto the fitting 32', the biopsy needle 80 functions substantially the same as herein before described in connection with the biopsy needle unit 12.

From the foregoing, it will thus be apparent that the present invention comprises an improved disposable biopsy needle unit having several advantages over the prior art. One important advantage involves the use of a cross tab or non-circular fitting welded near the proximal end of the needle which is molded inside a solid hub portion of a plastic handle to obtain effective structural integrity at that junction while achieving cost savings. Similar purposes are served by the use of a turned proximal end within the molded cap of the stylet. Another advantage involves the use of locking ears on the Luer fitting for positively but releasably securing a syringe or other aspiration device directly to the biopsy needle by means of a simple twisting motion. Other advantages will be evident to those skilled in the art.

Although particular embodiments of the invention have been illustrated in the accompanying Drawings and described in the foregoing Detailed Description, it will be understood that the invention is not limited only to the embodiments disclosed, but is intended to embrace any alternatives, equivalents, modifications and/or rearrangements of elements falling within the scope of the invention as defined by the following claims.

What is claimed is:

1. A biopsy needle unit, comprising:
    a straight cannula of substantially uniform cylindrical configuration over the major portion of its length and having distal and proximal ends, the distal end being tapered and bevelled;
    a tapered hollow fitting having distal and proximal ends with the distal end being connected to the proximal end of said cannula in coaxial relationship to define a longitudinal bore therethrough;
    a handle of generally T-shape having a distal end defining a central hub portion, and a proximal end defining oppositely extending lateral wing portions with a transverse recess between the wing portions opposite the hub portion;
    the hub portion of said handle being formed about the adjacent connected proximal and distal portions of said cannula and said fitting, respectively, with the proximal end of said fitting being disposed completely with in the recess of said handle and not extending beyond proximal surfaces of the wing portions;
    a removable stylet disposed in said cannula and said fitting;
    said stylet including a straight solid needle with a bevelled distal end and a turned proximal end, with a cap secured to the proximal end of the needle;
    the wing portions of said handle and the cap of said stylet having rounded proximal surfaces for manual comfort;
    means for releasably securing said stylet and said handle against relative rotational movement; and
    means defining structure secured between said cannula and said fitting within the hub portion of said handle for reinforcement against pushing and twisting forces during insertion of the biopsy needle unit.

2. The biopsy needle unit of claim 1, wherein said cannula is formed of stainless steel.

3. The biopsy needle unit of claim 1, wherein the central hub portion of said handle is of solid cross section tapered toward the distal end of said cannula.

4. The biopsy needle unit of claim 1, further including:
    oppositely-extending locking ears on the proximal end of said hollow fitting for releasable attachment to an aspiration syringe.

5. The biopsy needle unit of claim 1, wherein said stylet is of substantially uniform cylindrical configuration, and wherein said means for releasably securing said stylet and said handle against relative rotation comprises:

the cap of said stylet including an end portion enclosing the turned proximal end of the needle, and a tapered stem portion surrounding a portion of said needle adjacent the proximal end thereof and received in said fitting; and an offset lug extending in a generally longitudinal direction from the end portion of said cap received in an opening in said handle for positioning said needle within said cannula so that the bevelled distal ends thereof are substantially even to present a substantially smooth surface for inser- tion into a patient.

6. The biopsy needle unit of claim 1, wherein said reinforcement structure comprises a transverse flat tab of stainless steel externally- welded near the proximal end of said cannula, which is also of stainless steel.

7. A biopsy needle unit, comprising:

a straight cannula of substantially uniform cylindrical configuration having distal and proximal ends, the distal end being tapered and bevelled;

a tapered hollow fitting having distal and proximal ends with the distal end being connected to the proximal end of said cannula to define a longitudinal bore therethrough;

a transverse tab externally affixed to said cannula near the proximal end thereof;

a handle of generally T-shape including a distal end defining a central hub portion, and a proximal end defining oppositely extending lateral wing portions with a transverse recess between the wing portions opposites the hub portion.

the hub portion of said handle being molded about said tab and adjacent proximal and distal portions of said cannula and said fitting, respectively, with the proximal end of said fitting being dispsoed completely with in the recess between the wing portions of said handle and below proximal surfaces of the wing portions;

a removable stylet disposed within said cannula and said fitting;

said stylet including a straight needle of solid substantially uniform cylindrical configuration with a bevelled distal end, and a turned proximal end;

a cap secured to the turned proximal end of the stylet needle, said cap including a tapered distal stem portion snugly received in said fitting, and a rounded proximal end; and an offset longitudinal lug extending from said cap for receipt in a corresponding opening in the proximal end of said handle for positioning said needle within said cannula so that the bevelled distal ends thereof are substantially even to present a substantially smooth surface for insertion into a patient.

8. The biopsy needle unit of claim 7 wherein said cannula, said stylet needle, and said tab are formed of stainless steel, with said tab and said cannula being secured together by laser welding.

9. The biopsy needle unit of claim 7, wherein the central hub portion of said handle is of solid cross section tapered toward the distal end of said cannula.

10. The biopsy needle unit of claim 7, further including:

oppositely-extending locking ears on the proximal end of said hollow fitting for releasable attachment to an aspiration syringe.

* * * * *